United States Patent
Pardee et al.

(10) Patent No.: US 6,245,807 B1
(45) Date of Patent: Jun. 12, 2001

(54) TREATMENT OF HUMAN PROSTATE DISEASE

(75) Inventors: Arthur Pardee, Brookline; Chiang J. Li, West Roxbury, both of MA (US)

(73) Assignee: Dana-Farber Cancer Institute, Boston, MA (US)

(*) Notice: Subject to any disclaimer, the term of this patent is extended or adjusted under 35 U.S.C. 154(b) by 0 days.

(21) Appl. No.: 09/028,400

(22) Filed: Feb. 24, 1998

Related U.S. Application Data

(63) Continuation of application No. PCT/US96/13335, filed on Aug. 19, 1996, which is a continuation of application No. PCT/US96/13336, filed on Aug. 23, 1996.
(60) Provisional application No. 60/002,829, filed on Aug. 25, 1995, and provisional application No. 60/002,828, filed on Aug. 24, 1995.

(51) Int. Cl.⁷ .................. C07D 311/82; C07D 311/92
(52) U.S. Cl. .................... 514/454; 549/388; 549/390
(58) Field of Search ..................... 514/454; 549/388, 549/390

(56) References Cited

U.S. PATENT DOCUMENTS

| | | | |
|---|---|---|---|
| 5,763,625 | * 6/1998 | Boothman et al. | 549/390 |
| 5,872,150 | * 2/1999 | Elbrecht et al. | 514/563 |

FOREIGN PATENT DOCUMENTS

| | | | |
|---|---|---|---|
| WO 94/04145 | 3/1994 | (WO) | A61K/31/35 |
| WO 97/07797 | * 3/1997 | (WO) | A61K/31/35 |

OTHER PUBLICATIONS

S.M. Planchon, et al., Proc. Am. Assoc. Cancer Res. Annu. Meet., vol. 37, pp 429–430. XP000611540 #2933 (Apr. 1996).
C.J. Li, et al., Cancer Research, vol. 55, No. 17 pp 3712–3715. XP000611542 (Sep. 1995).
S.M. Planchon, et al., Cancer Res., vol. 55, No. 17 pp 3706–3711. XP000611541 (Sep. 1995).
Martikainen et al. Programmed death of nonproliferating androgen–independent prostatic cancer cells. Cancer Research, 51, pp. 4963–4700. (Sep. 1991).*
Schaffner–Sabba et al. β–lapachone: Synthesis and derivatives and activities in tumor models. J. Med. Chem. 27 (8), pp. 990–994. (1984). No month found.*

Singh et al. Conversion of lapachol to rhinacanthin–A and other cyclized products. Z. Naturforschung B: Chem. Sci. 47 (7), pp. 1031–1033. (1992). No month found.*

* cited by examiner

Primary Examiner—Ardin H. Marschel
Assistant Examiner—Marjorie A. Moran
(74) Attorney, Agent, or Firm—Nixon Peabody LLP

(57) ABSTRACT

We have now discovered that unexpectedly compounds of the following formulae I or 11 can be used to selectively stimulate the death of mammalian prostate cells, including both epithelial cell and prostate cancer cells, and thus are useful in treating prostate diseases:

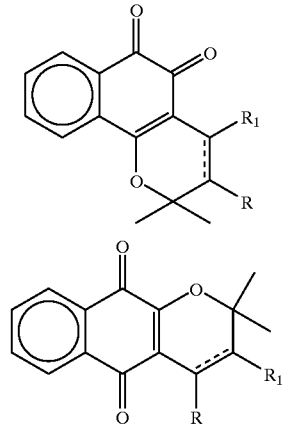

wherein R and $R_1$ are each independently selected from the group consisting of hydrogen, hydroxy, thio (SH), halogen, substituted and unsubstituted alkyl, substituted and unsubstituted alkenyl, substituted and unsubstituted aryl, and substituted and unsubstituted alkoxy, and salts thereof, wherein the dotted double bond between the ring carbons to which R and $R_1$ are bonded represent an optional ring double bond. Preferred compounds of formula I include those in which at least one of the substituents R and $R_1$ is hydrogen and/or at least one of said substituents is allyl. Specifically preferred compounds include β-lapachone (i.e., R and $R_1$ both being hydrogen), allyl-β-lapachone, particularly 3-allyl-β-lapachone (i.e. R being allyl and $R_1$ being hydrogen) and 3-bromo-β-lapachone (i.e. R being bromo and $R_1$ being hydrogen).

6 Claims, 5 Drawing Sheets

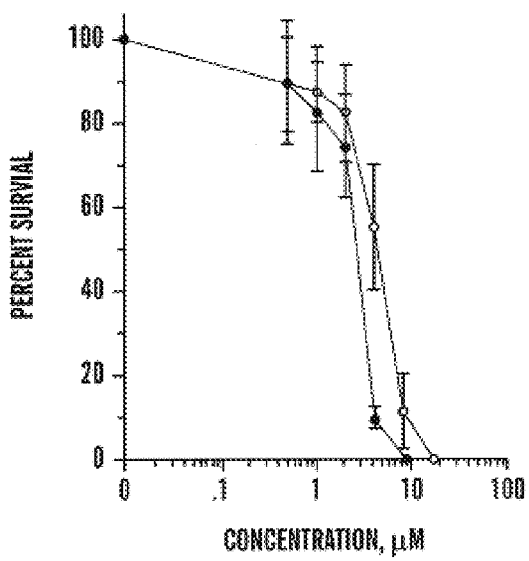
FIG. 1
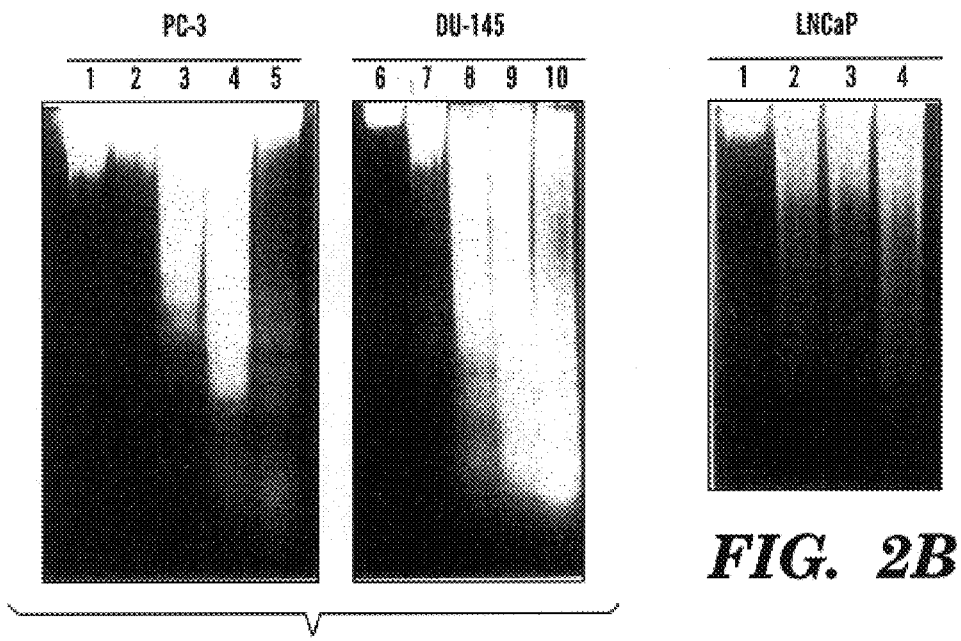
FIG. 2A
FIG. 2B
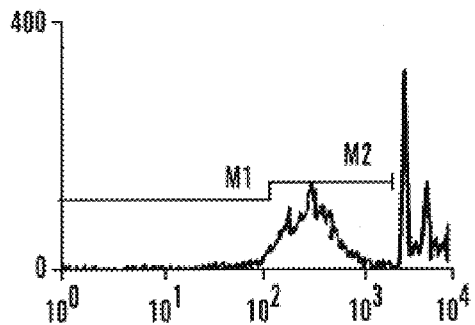
FIG. 2C
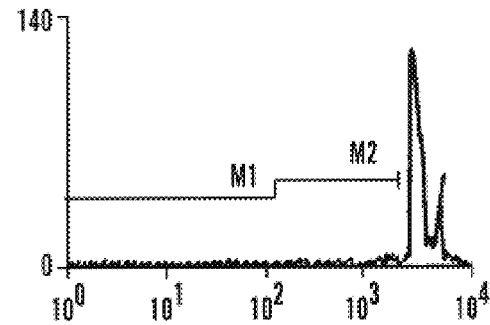
FIG. 2D

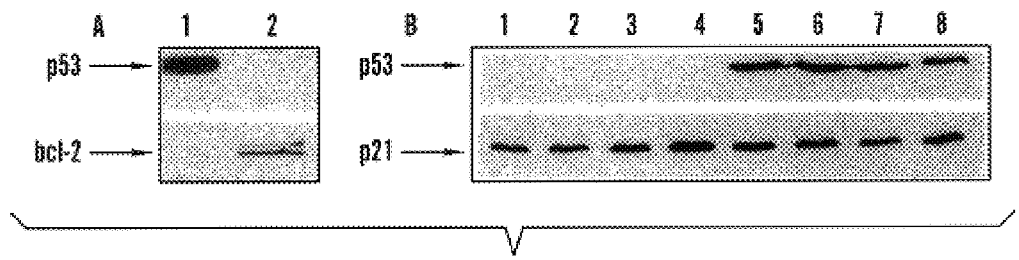
FIG. 3
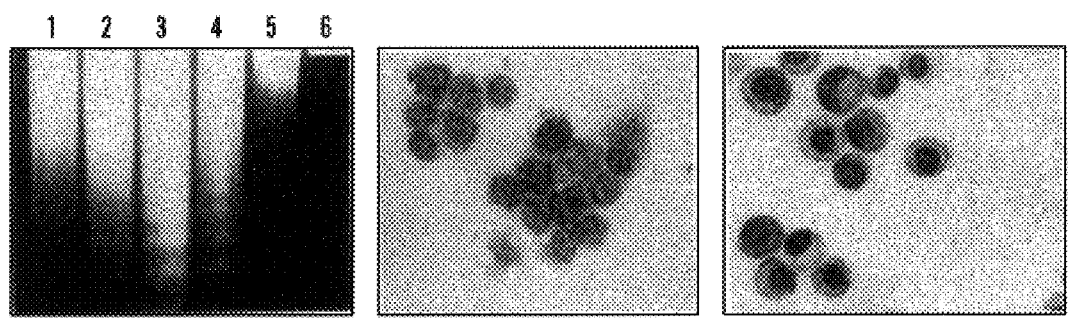
FIG. 4A  FIG. 4B  FIG. 4C

TREATMENT OF HUMAN PROSTATE DISEASE

This is a continuation of co-pending International Application PCT/US96/13335, filed on Aug. 19, 1996 and a con of PCT/US96/13336 Aug. 23, 1996 and which designated the U.S.

This application claim benefit to provisional application 60/002,829 filing date Aug. 25, 1996, which claim benefit to provisional application 60/002,828 filed date Aug. 24, 1995.

BACKGROUND OF THE INVENTION

The present invention is directed to a method of treating an individual suffering from benign prostate hyperplasmia and prostate cancer.

The prostate gland produces several components of semen in blood and several regulatory peptides. The prostate gland comprises stroma and epithelium cells, the latter group consisting of columnar secretory cells and basal non-secretory cells. The proliferation of these basal cells, as well as stroma cells gives rise to benign prostatic hyperplasmia (BPH) which is one common prostate disease. BPH is a progressive condition which is characterized by the nodular enlargement of the prostatic tissue resulting in obstruction of the urethra. This results in increased frequency of urination, noncuria, poor urine stream, and hesitation or delay in starting the urine flow. Consequences of BPH can include hypertrophy of bladder smooth muscle, decompensated bladder, and increased incidence of urinary tract infection. The development of BPH is considered to be an escapable phenomenon for the aging male population. BPH is observed in approximately 70% of males over the age of 70. Currently in the United States, the method of choice for treating BPH is surgery, e.g., transurethral recession of the prostate. There is no adequate therapeutic drug treatment for BPH.

Another common prostate disease is prostatic adenocarcinoma (CaP) or androgen independent prostate cancer, which involves malignant transformation of epithelial cells in the peripheral region of the prostate gland. Androgen independent prostate cancer is presently the most common cancer in men in the United States with 38,000 deaths anticipated for the USA in 1994, and is a significant condition worldwide. Approximately 50% of patients are presented with metastatic disease. However, the only existing treatment for metastatic disease is hormonal therapy, which is not curative. Thus, the metastatic disease is typically fatal.

Hormonal therapy consisting of different approaches to blocking the action of androgen on the prostate tumor is effective in controlling only the growth of tumor cells that depend on androgen for growth (hormone-dependent tumor). Unfortunately, hormone-dependent tumor inevitably progresses to more advanced hormone-independent tumor, which cannot be controlled by current treatment. Difficulties in treating prostate cancer arise from a variety of reasons. Although such androgen ablation is a standard therapy for metastatic prostate cancer it is rarely entirely successful because in most individuals the cancer is heterogeneous comprising both androgen dependent and androgen independent cancer cells. Thus, the therapy does not eliminate the androgen independent cells.

Chemotherapy, which has been used to treat a number of other cancers, has not proven successful. This is because the vast majority of these androgen independent cells are not actively proliferating and standard chemotherapeutic agents work by selectively killing actively proliferating cells.

Radiation therapy, which also is selective for rapidly proliferating cells, has also not proven effective. Surgery has also not proven an effective means for treating advanced disease states. Accordingly, it would be desirable to have new methods for stimulating the death of these slow proliferating cancer cells. It would be particularly desirable to have a new means of treating individuals suffering from prostate cancer, particularly androgen independent cancer.

$\beta$-lapachone (3,4dihydro-s,3-dimethyl-2H-naphthol[1,3-b]pyran-5,6-clone) is a simple plant product with a chemical structure different from currently used anti-cancer drugs. It is obtained by sulfuric acid treatment of the naturally occurring lapachol, which is readily isolated from Tabebuia avellanedae growing mainly in Brazil, or is easily synthesized from lomatiol, isolated from seeds of lomatia growing in Australia (Hooker, S., et. al., *J. Am. Chem. Soc.*, 58:1181–1190 (1936); Goncalves de Lima, O, et al., *Rev. Inst. Antibiot. Univ. Recife.* 4:3–17 (1962)).

$\beta$-lapachone has been shown to have a variety of pharmacological effects. $\beta$-lapachone is a topoisomerase I inhibitor but acts by a different mechanism than camptothecin. Numerous $\beta$-lapachone derivatives have been synthesized and tested as anti-viral and anti-parasitic agent (Goncalves, A. M., et al., *Mol. Biochem. Perasitology*, 1:167–176 (1980); Schaffner-Sabba, K., et al., *J. Med. Chem.*, 27:990–994 (1984); Li, C., et al., *Proc. Natl. Acad. Sci. USA*, 90:187–1842 (1993)). $\beta$-lapachone and its derivatives, e.g. 3-allyl-$\beta$-lapachone, show anti-trypanosomal effects (Goncalves, A. M., et al., supra), the mechanism of which is unclear. It significantly prolongs the survival of mice infected with Rauscher leukemia virus, probably through inhibition of reverse transcriptase (Schaffner-Sabba, K., et al., supra; Schuerch, A. R., et al., *J. Biochem.*, 84:197–205 (1978)). We taught that $\beta$-lapachone also inhibits gene expression directed by the long terminal repeat (LTR) of the human immunodeficiency virus type 1, and viral replication (Li, C., et al., supra). $\beta$-lapachone has also been shown to be a DNA repair inhibitor which sensitizes cells to DNA damaging agents (Boorstein, R. J., et al., *Biochem. Biophys. Res. Commun.*, 118:828–834, (1984); Boothman, D. A., et al., *J. Cancer Res.*, 49:605–612 (1989)). $\beta$-lapachone is well tolerated in dogs, rats, mice, and chickens. The maximum tolerated dose, when given p.o daily for one month, is 200 mg/kg in rats, and 100 mg/kg in dogs. Higher doses cause gastric ulceration and loss of erythrocytes, but not signs of bone marrow suppression (Ciba-Geigy, personal communication). The previous experience with this compound in humans has been limited.

SUMMARY OF THE INVENTION

We have now discovered that unexpectedly compounds of the following formulae I and II can be used to selectively stimulate the death of mammalian prostate cells, including both epithelial cell and androgen dependent and independent prostate cancer (CaP) cells, and thus are useful in treating prostate diseases:

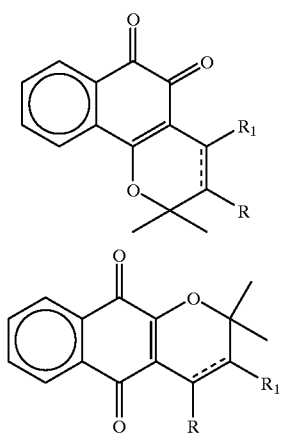

wherein R and $R_1$ are each independently selected from the group consisting of hydrogen, hydroxy, sulfhydryl, alogen, substituted and unsubstituted alkyl, substituted and unsubstituted alkenyl, substituted and unsubstituted aryl, and substituted and unsubstituted alkoxy, and salts thereof, wherein the dotted double bond between the ring carbons to which R and $R_1$ are bonded represent an optional ring double bond. Preferred compounds of formula I include those in which at least one of the substituents R and $R_1$ is hydrogen and/or at least one of said substituents is allyl. Specifically preferred compounds of formula I include β-lapachone (i.e., R and $R_1$ both being hydrogen), allyl-β-lapachone, particularly 3-allyl-β-lapachone (i.e. R being allyl and $R_1$ being hydrogen) and 3-bromo-β-lapachone (i.e. R being bromo and $R_1$ being hydrogen).

BRIEF DESCRIPTION OF THE DRAWINGS

FIG. 1 shows the effect of β-lapachone on survival of human prostate cancer cells O, PC-3 cells; DU145 cells. Cell survival was determined by the colony formation assay described below.

FIGS. 2A, 2B, 2C and 2D show induction of apoptosis by β-lapachone in human prostate cancer cells. DNA laddering, typical feature of apoptosis, was induced in PC-3, D 145 (2A) and LNCaP cells (2B). In 2A, cells were treated with 4 μM, β-lapachone for 4 hours, followed by incubation in drug-free medium for 4 hours (lane 2,7), 12 hours (lane 3,8), 20 hours (lane 4,9), 44 hours (lane 5, 10). As controls, cells were treated with equal volume of DMSO (lane 1,6). DNA was extracted and subjected to electrophoresis. In 2B, LNCaP cells were treated with β-lapachone for 4 hours at concentrations of 0 μM (lane 1), 0.5 μM (lane 2), 2 μM (lane 3), 4 μM (lane 4), followed by drug free incubation for 20 hours. To quantify apoptotic fraction, LNCaP cells were treated with or DMSO (2C) or 8 μM β-lapachone (2D) for 1 hour, followed by incubation in drug-free media for 23 hours before they were subjected to flow cytometric analysis.

FIG. 3 shows lack of correlation between β-lapachone induced apoptosis and the expression of p53 and bcl-2. A. Expression pattern of p53 and bcl-2 in DU-145 cells (lane 1) and PC-3 cells (lane 2). B,β-lapachone did not induce expression of p53 and p21. Lane 1 to 4: PC-3 cells; lane 5 to 8: DU-145 cells. Cells were treated with DMSO (lane 1,5), or β-lapachone at 2 μM (lane 2,6), 4 μM (lane 3, 7) and 8 μM (lane 4, 8) for 1 hour, followed by incubation in drug free media for 23 hours. Expressions of p53, p21, and bcl-2 were determined by Western blot assay as described below.

FIGS. 4A, 4B, and 4C shows induction of apoptosis (A) and differentiation in HL-60 cells (B,C) by β-lapachone. In 4A, HL-60 cells were treated with 8 μM -lapachone for 24 hours (lane 1). 16 hours (lane 2), 8 hours (lane 3), 4 hours (lane 4), 2 hours (lane 5), 0 hours (lane 6). Cellular DNA was extracted and subjected to gel electrophoresis. To analyze morphological changes induced by β-lapachone, HL-60 cells were treated with ethanol (1/1000, v/v) (4B) or 0,8 pM β-lapachone dissolved in ethanol (4C) for 6 days before harvest. A thin film of cells were spread on a slide, and stained with modified Wright-Giemsa Stain (Sigma).

DETAILED DESCRIPTION OF THE INVENTION

Figure 5:
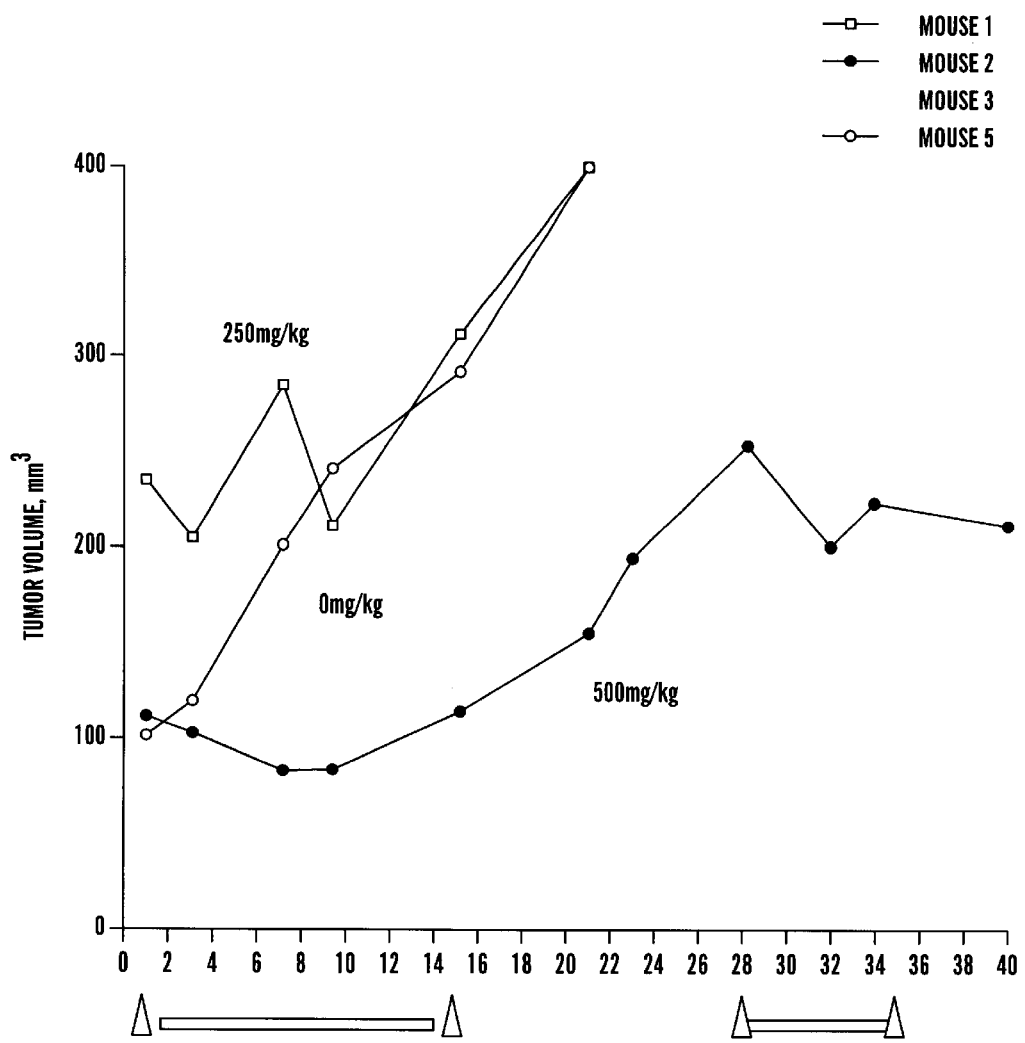
FIG. 5 shows the effect of β-lapachone on tumor volume. The bar represents episodes of administration of β-lapachone.

We have now discovered that unexpectedly compounds of the following formulae I and II can be used to stimulate the death of mammalian prostate cells including both epithelial and androgen dependent and independent prostate cancer (CaP) cells. The mammal is preferably a human. Thus, the compounds having the following formulae are useful in treating prostate diseases:

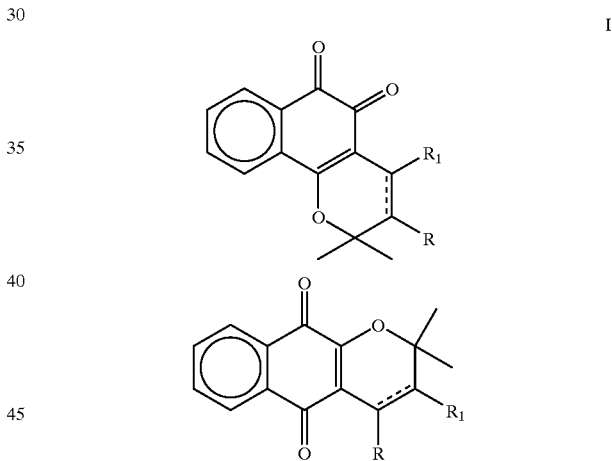

wherein R and $R_1$ are each independently, selected from the group consisting of hydrogen, hydroxy, sulthyryl (SH), halogen (e.g. fluoro, chloro and bromo), substituted and unsubstituted aryl, substituted and unsubstituted alkenyl, substituted and unsubstituted alkyl and substituted and unsubstituted alkoxy, and salts thereof, wherein the dotted double bond between the ring carbons to which R and $R_1$ are bonded represent an optional ring double bond. The alkyl groups preferably have from 1 to about 15 carbon atoms, more preferably from 1 to about 10 carbon atoms, still more preferably from 1 to about 6 carbon atoms. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to 15 carbon atoms, more preferably from 2 to about 10 carbon atoms, still more preferably from 2 to about 6 carbon atoms. Especially preferred alkenyl groups have 3 carbon atoms (i.e., 1-propenyl or 2-propenyl), with the allyl moiety being particularly preferred. Phenyl and naphthyl are generally preferred aryl groups. Alkoxy groups include those alkoxy groups having one or more oxygen linkage and preferably have from 1 to 15 carbon atoms, more preferably from 1 to about 6 carbon atoms. Said substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from 6 to 10 carbon atoms, halogen such as fluoro, chloro and bromo, and N, O and S, including heteroalkyl, e.g., heteroalkyl having one or more of said hetero atom linkages (and thus including alkoxy, aminoalkyl and thioalkyl) and from 1 to 10 carbon atoms or from 1 to 6 carbon atoms.

As the experiments discussed below show, the compounds of formulae I and II are useful in suppressing survival in human ovary and breast cells, and are thus useful in treating ovarian and breast cancer.

Compounds of formulae I and II can readily be made or obtained. (See Pardee, A., et al., *Cancer Research*, 49, 1–8 (1989); Schaffner-Sabba, K., et al., *Journal of Medicinal Chemistry*, 27, no. 8 990–994 (1984); S. Hooker, 58, 1181–1197 (1936).

Preferred compounds of formula I include β-lapachone, 3-allyl-β-lapachone, 3-bromo-β-lapachone and 3-OH-β-lapachone, 3-allyl-β-lapachone and 3-bromo-β-lapachone are more preferred.

Preferred compounds of formula II include 3-bromo-alpha-lapocleone (compound 4 of Table 1).

We have tested a variety of human cancer cells for their sensitivity to compounds of formulae I and II, e.g. β-lapachone, a novel inhibitor of DNA topoisomerase I (Li, C. J., et al., supra). Human prostate cancer cells were the cancer cells that was most sensitive to β-lapachone and its derivatives, these compounds exhibiting enhanced death rates. We believe these cells were induced to undergo a process of programmed cell death (apoptosis) specifically activated in prostate cells after they are deprived of testosterone (Martikainen, P., et al., *Cancer Res.* 51:4693–4700 (1991)). Results in the nude mouse model demonstrate that compounds of formulae I and II such as β-lapachone can inhibit human prostate tumor growth. This compound also causes suppression of survival, albeit at slightly higher concentrations, in human ovary and breast cells. However, typical apoptosis was not detected in any other human cancer cells of epithelial origins including colon, kidney, lung, breast, or ovary exposed to the drug other than the prostate cells. Human hematopoietic leukemia cells (HL-60) were induced to undergo either apoptosis or differentiation depending on the concentration used.

The prevalence of p53 inactivation and/or bcl-2 expression in human tumors is generally believed to be at least partially responsible for the general ineffectiveness of current chemo- and radiation therapy for cancer (Berchem, G. J., et al., *Cancer Res.* 55:735–738 (1995); Lowe, S., et al., *Science* 266:807–810 (1994)). It is thus important to develop novel anti-cancer drugs that induce cell death in a p53 independent manner. One way such compounds could work is through activation of p53 targeting genes, e.g. p21 (SDI1/WAF1/Cip1), by a p53 independent pathway (Johnson, M., et al. *Mol. Carcinogenesis* 11:59–64 (1994)i. We have shown that compounds of formulae I and II such as β-lapachone, and its derivatives induced apoptosis in the absence of p53 expression (FIG. 3A) indicating that it may be p53 independent. There was no significant induction of p53 and p21 (FIG. 3B) in human prostate cancer cells during apoptosis, suggesting that the induced apoptosis occurs independent of the p53 pathway. β-lapachone and its derivatives induced cell death that also did not correlate with bcl-2 expression and was not protected by ectopically overexpressed bcl-2. These results thus indicate the existence of a cell death program independent of both p53 and bcl-2 can be activated by compounds of formulae I and II such as β-lapachone and its derivatives.

We have also treated human non-tumor prostate epithelial cells with β-lapachone and found that their are proliferative ability was completely halted at concentrations as low as 1–2 μM. Epithelial cancer cells from colon, kidney, lung, and other cell lines, are generally resistant to β-lapachone (10 to 100 μM) (Boorstein, et al., *Biochem. Biophys. Res. Commun.* 118, 828–834 (1984); Boothman, et al. *Cancer Res.* 47, 5361–5366 (1987)).

In general, for the treatment of androgen independent prostate cancer, a suitable effective dose of one or more compounds of formulae I or II will be preferably in the range of 10 to 500,000 μg per kilogram body weight of recipient per day, more preferably in the range of 1000 to 50,000 μg per kilogram body weight per day, most preferably in the range of 5000 to 25,000 μg per kilogram body weight per day. The desired dose is suitably administered once or several more sub-doses administered at appropriate intervals throughout the day, or other appropriate schedule. These sub-doses may be administered as unit dosage forms, for example, containing 1 to 20,000 μl, preferably 10 to 10,000 μg per unit dosage form.

Accordingly, one would use an effective amount of these compounds in a method to stimulate the death of prostate tumor cells, particularly androgen independent prostatic tumor cells. One would select a subject having prostatic tumor cells and administer an effective amount of one of the compounds of formulae I or 11 such as 3-allyl-β-lapachone, 3-halo-β-lapachone or β-lapachone to treat the prostatic tumor cell. Preferably, the subject is a human. Still more preferably, the human has CaP.

In treating metastatic disease, because selective nature of the compounds of formulae I and II, one can administer the compounds intravenously.

Administration of the compounds of the invention may be by any suitable route including oral, rectal, nasal, vaginal, topical (including buccal and sublingual), and parenteral (including subcutaneous, intramuscular, intravenous and intradermal) with oral or parenteral being preferred. It will be appreciated that the preferred route may vary with, for example, the condition and age of the recipient.

The administrative ingredients may be used in therapy in conjunction with other medicaments.

While one or more compounds of formulae I or II may be administered alone, they also may be present as part of a pharmaceutical composition. The compositions of the invention comprise at least one compound of formulae I or II together with one or more acceptable carriers thereof and optionally other therapeutic ingredients, including those therapeutic agents discussed supra. The carrier(s) must be "acceptable" in the sense of being compatible with the other ingredients of the formulation and not deleterious to the recipient thereof.

The compositions include those suitable for oral, rectal, nasal, topical (including buccal and sublingual) or parenteral (including subcutaneous, intramuscular, intravenous and intradermal) administration. The compositions may conveniently be presented in unit dosage form, e.g., tablets and sustained release capsules, and in liposomes and may be prepared by any methods well known in the art of pharmacy.

Such methods include the step of bringing into association the to be administered ingredients with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gels and pastes comprising one or more compounds of formulae I or II and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

To ensure solubility, the compounds are preferably dissolved in a non-ionic solubilizer such as an ethylene oxide ester-ether and fatty acid glycerides commercially available as Cremphor EL (BASF).

It should be understood that in addition to the ingredients particularly mentioned above the formulations of this invention may include other agents conventional in the art having regard to the type of formulation in question, for example, those suitable for oral administration may include flavoring agents.

All documents mentioned herein are incorporated herein by reference.

The present invention is further illustrated by the following examples. These examples are provided to aid in the understanding of the invention and are not construed as a limitation thereof.

EXAMPLES

General Comments

The following reagents and procedures were employed as specified in the examples.

Chemicals

β-lapachone was kindly provided by Dr. A. Matter (CIBA-GEIGY Ltd., Switzerland). It was dissolved in dimethyl sulfoxide (DMSO) at 20 mM concentration, aliquoted, and kept at −20° C.

Cell Cultures

All cell lines used in this study are obtained from the American Type Culture Collection (Rockville, Md.) unless specified otherwise. Cells were maintained at 37° C. in 5% CO2 in complete humidity. Human prostrate tumor cells PC-3, DU145, and LNCaP were grown in Dulbecco's modified Eagle's Medium (Life Technologies, Inc.) supplemented with 10% FCS and 2 mM L-glutamine. HL-60 (human promyelocytic leukemia cell line) was cultured in RPMI medium with 10% heat inactivated FCS. MCF-7 and 21 MT (human breast epithelial cell line), kindly provided by Dr. R. Sager (Dana-Farber Cancer Institute, Boston, Mass.), were cultured in MEM alpha medium (Life Technologies, Inc.) supplemented with 10% FCS, 2 mM L-glutamine, and 1 mg/ml insulin. AD 2780s (human ovary carcinoma), a generous gift from Dr. K. J. Scanlon (City of Hope Medical Center, Duarte), 293 (human kidney epithelial cell line), SW1116 (human colon adenocarcinoma), and human lung carcinoma cell lines (H596, H520) were cultured in Dulbecco's modified Eagle's medium (Life Technologies, Inc.) supplemented with 10% FCS and 2 mM L-glutamine. Hela and Hela-bcl-2 cells (Meikrantz, W., et al., *Proc. Natl. Acad. Sci. USA*, 91:3754–3758 (1994), kindly provided by Drs. W. Meikrantz and R. Schlegel (Harvard School of Public Health, Boston, Mass.), were cultured in Dulbecco's modified Eagle's medium (Life Technologies, Inc.) supplemented with 10% FCS, 2 mM L-glutamine, and 800 µg/ml of G418.

Colony Formation Assay

Exponentially growing cells were seeded (2000 cells/dish) in 60 mm culture dishes and allowed to attach for 48 hours. β-lapachone was added in less than 5 µl volume (corresponding to a final DMSO concentration of less than 0.1%) directly to dishes from concentrated working solutions in DMSO. Control dishes received DMSO alone at equal volume. After 1 to 4 h, cells were rinsed and drug free medium was added to the cells. Cultures were observed daily for 10 to 20 days, cells were fixed and stained with modified Wright-Giemsa Stain (Sigma). Colonies of greater than 30 cells were scored as survivors.

Agarose Gel Electrophoresis of Apoptotic DNA

The method of Wesselborg, S., et al., *J. Immunol.*, 150:4338 (1993) was used. Cells were treated with β-lapachone, and then incubated in drug-free media. They were harvested and lysed in 50 mM Tris-HCl, 10 mM EDTA, 0.5% SDS, 0.5 mg/ml proteinase K, and 0.15 ng/ml RNase. The supernatant of the cell lysate was loaded onto a 2% agarose gel. The electrophoresis was carried out at 24 V for 16 hours. The gel was stained with ethidium bromide. A Polaroid picture was taken after detaining the gel for 1 hour.

Flow Cytometry Analysis

Cytofluorometric analysis of apoptosis and cell cycle analysis was performed by propodium iodide staining of nuclei as reported previously (Li, C. J., et al., *Science* 268:429–431 (1995)).

Western Blot Analysis

Nuclear extract was prepared from exponentially growing cells (Dignam, J. D., et al., *Nucleic Acids Res.*, 11:1475 (1983)). The ECL assay system was used to detect p53 and bcl-2 levels. Briefly, nuclear protein samples (10 µg per sample) were electrophoresed in a sodium dodecyl sulfate-polyacrylamide gel and then electrophoretically transferred to a nitrocellulose membrane. The blot was blocked, washed, and incubated with p53, bcl-2, or p21 (Cipl/Waf1) antibody (Oncogene Science, Cambridge, Mass.) at 1:1000 dilution. The filter was then incubated with a secondary antibody that was conjugated with horseradish peroxidase. Finally, the filter was developed with detection reagents (RPN 2109:Amersham) and exposed to a hyperfilm-ECL (RPN 2103).

Animal Administration

In the in vivo animal experiments, β-lapachone was formulated into solution with Cremophor EL (BASF).

Example 1

Effects of β-Lapachone on Prostate Weight

Rats in the treated group received β-lapachone at 50 mg/kg l.p.. After treatment the average prostate weight was 345±72 g for control rats, and 203±19 g treated animals. Statistical analysis showed a signficant decrease in prostate weight (p0.000002). These results demonstate that -lapachone indued shrinkage of the prostate gland.

Example 2

Effects of β-Lapachone on Survival of Human Cancer Cells

Human carcinoma cell lines of different histotypes were used to test the anti-survival effect of β-lapachone. Androgen independent human prostate tumor cells PC-3 and DU145 were treated with β-lapachone in vitro. Cell survival was determined by colony formation assay, β-lapachone inhibits proliferation of both cell lines with an $IC_{100}$ of 4 to 8 µM (FIG. 1). LNCaP cells were equally sensitive to β-lapachone. 21 MT (a human breast carcinoma cell line) and AD2780s (a human ovary carcinoma cell line) were also relatively sensitive to the antiproliferative effect of β-lapachone ($IC_{100}$, 16 µM). Proliferation of SW116, a human colon adenocarcinoma cell line, was not significantly inhibited by β-lapachone up to 128 µM, the maximum concentration used. Other cell lines tested, which included H596, H520 (human lung carcinoma cell lines) and 293 (a human kidney epithelial cell line) were also relatively resistant to β-lapachone ($IC_{100}$>32 µM).

Seventeen derivatives of β-lapachone were tested in PC-3 and DU145 cells in the manner described above. 3-allyl-β-lapachone and 3-bromo-β-lapachone were found to be more active than β-lapachone against prostate cells (Table 1).

TABLE 1

Antisurvival effect of β-lapachone and its derivatives against human prostate cancer cells

| β-lapachone and derivatives | Activity |
|---|---|
| 1 | +/− |
| 2 | +/− |
| 3 | +/− |
| 4* | +++ |
| 5 | +/− |

TABLE 1-continued
Antisurvival effect of β-lapachone and its derivatives against human prostate cancer cells
| β-lapachone and derivatives | Activity |
|---|---|
| 6 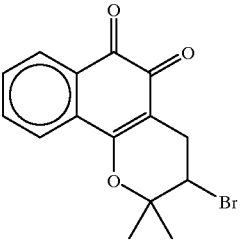 | ++++ |
| 7 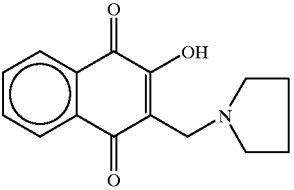 | +/− |
| 8 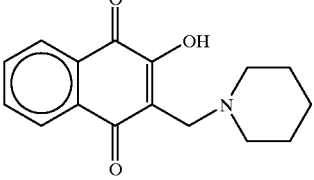 | +/− |
| 9 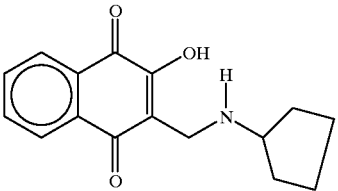 | +/− |
| 10 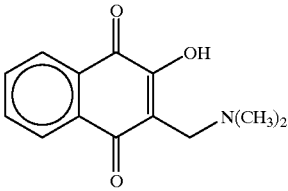 | +/− |
| 11 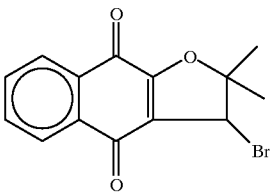 | +/− |
| 12* 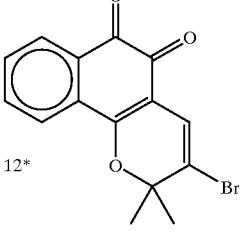 | ++ |
| 13 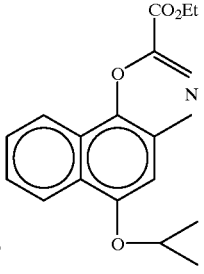 | +/− |
| 14 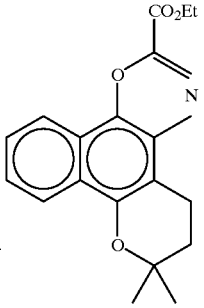 | +/− |
| 15 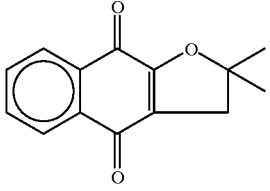 | +/− |
| 16 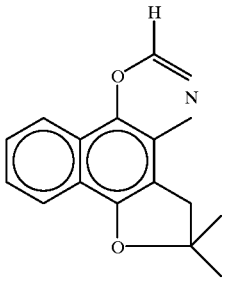 | +/− |

TABLE 1-continued

Antisurvival effect of β-lapachone and its derivatives against human prostate cancer cells

| β-lapachone and derivatives | Activity |
|---|---|
| 17 (structure) | +/− |
| 18* (structure) | +/− |
| 19* (structure) | ++ |

*Compound of the present invention.

Example 3

Induction of Apoptosis by β-Lapachone in Human Prostate Cancer Cells

Extensive cell death was observed in proliferating human prostate cancer cells after treatment with β-lapachone. To determine whether this cell death occurs through necrosis or apoptosis, cells were harvested by trypsinization and their genomic DNA was subjected to gel electrophoresis. As shown in FIGS. 2A and 2B, β-lapachone induced a typical DNA laddering in human prostate cancer cells, consistent with cell death by apoptosis, a process that is specifically activated in prostate cells after they are deprived of testosterone (Kyprianou, N., et al., Cancer Surv., 11:265–77, (1991)). This β-lapachone induced apoptosis was observed in every prostate cell line tested, including PC-3, DU 145, and LNCaP. To test whether quiescent cells are similarly sensitive to β-lapachone, both PC-3 and DU145 cells were serum starved for 48 hours before drug treatment. Apoptosis was similarly induced in non-proliferating cells (data not shown). To determine the percentage of apoptotic cells, the fraction of subG1 cells was quantitated with flow cytometry analysis. As shown in FIG. 2C, β-lapachone induced apoptosis in 68% of LNCaP cells by 24 hours after initial treatment with β-lapachone. In PC-3 cells, apoptosis occurs in 62% by 24 hours (data not shown). Apoptosis, as determined by DNA laddering and chromosome condensation, was not detected in β-lapachone treated 21-MT (human breast epithelial cell line), H520 (human lung carcinoma cell lines), SW1116 (human colon adenocarcinoma), A2780s (human ovary carcinoma) cells.

Example 4

Apoptosis Induced by β-Lapachone is Independent of Expression of p53 and bcl-2.

Expression of bcl-2 has been implicated in the resistance of cancer cells to chemotherapeutic drugs including prostate cells (Berchem, G. J., et al., Cancer Res. 55:735–738 (1995)). To determine whether apoptosis in prostate cancer cells is due to lack of bcl-2 expression, we measured bcl-2 expression by Western blot assay. As shown in FIG. 3, bcl-2 expression is high in PC-3 and low in DU145 cells, which does not correlate with their sensitivity to β-lapachone induced apoptosis. Hela cells with ectopic overexpression of bcl-2 (hela-bcl-2) (Meikrantz, W., et al., supra) was not significantly resistant to β-lapachone in comparison with its parental cell line (IC100 was 16 $\mu$M in parental cells, and 32 $\mu$M in Hela-bcl-2 cells) (data not shown).

p53 status has been shown to be important for apoptosis in cancer cells provoked by ionizing radiation and chemotherapeutic drugs (Lowe, S., et al., Science 266:807–810 (1994)). p 53 was expressed in DU145 cells, but was not detectable in PC-3 cells (FIG. 3A), although apoptosis was induced in both cell lines (FIG. 2A). β-lapachone treatment did not significantly induce expression of p53 (FIG. 3B). These results suggest that apoptosis induced by β-lapachone is not dependent on P53 expression. Expression of p21 is not significantly upregulated in prostate cancer cells undergoing apoptosis (FIG. 3B).

The effect of β-lapachone was also tested in hematopoietic cancer cells. Treatment of HL-60 (p53 -), a human leukemia cell line, with β-lapachone also induced apoptosis. Chromosomal laddering was detectable with 4 hours after β-lapachone treatment (FIG. 4A). At sub-apoptotic doses, β-lapachone induced an increase in the G1 fraction (data not shown) and morphological in HL-60 cells (FIG. 4B).

Example 5

Inhibition of Human Prostate Tumor Growth In Vivo

β-lapachone was tested against human prostate tumor in nude mice. A hormone refractory human prostate adenocarcinoma cell line (PC-3) was inoculated into nude mice. Treatment was initiated when tumor reached 100 to 250 mm$^3$. Without drug treatment (mouse 5), the tumor grew rapidly and the mouse died when the tumor reached about 400 mm$^3$ (FIG. 5). β-lapachone, given at 500 mg/kg, stopped tumor growth (mouse 2, FIG. 5). At intermediate dosage (250 mg.kg, mouse 1 and 3), β-lapachone also showed intermediate inhibition on tumor growth (FIG. 5). Mouse 4 did not develop an appreciable tumor mass under the treatment with β-lapachone (500 mg/kg). No sign of drug toxicity was observed.

Figure 6:
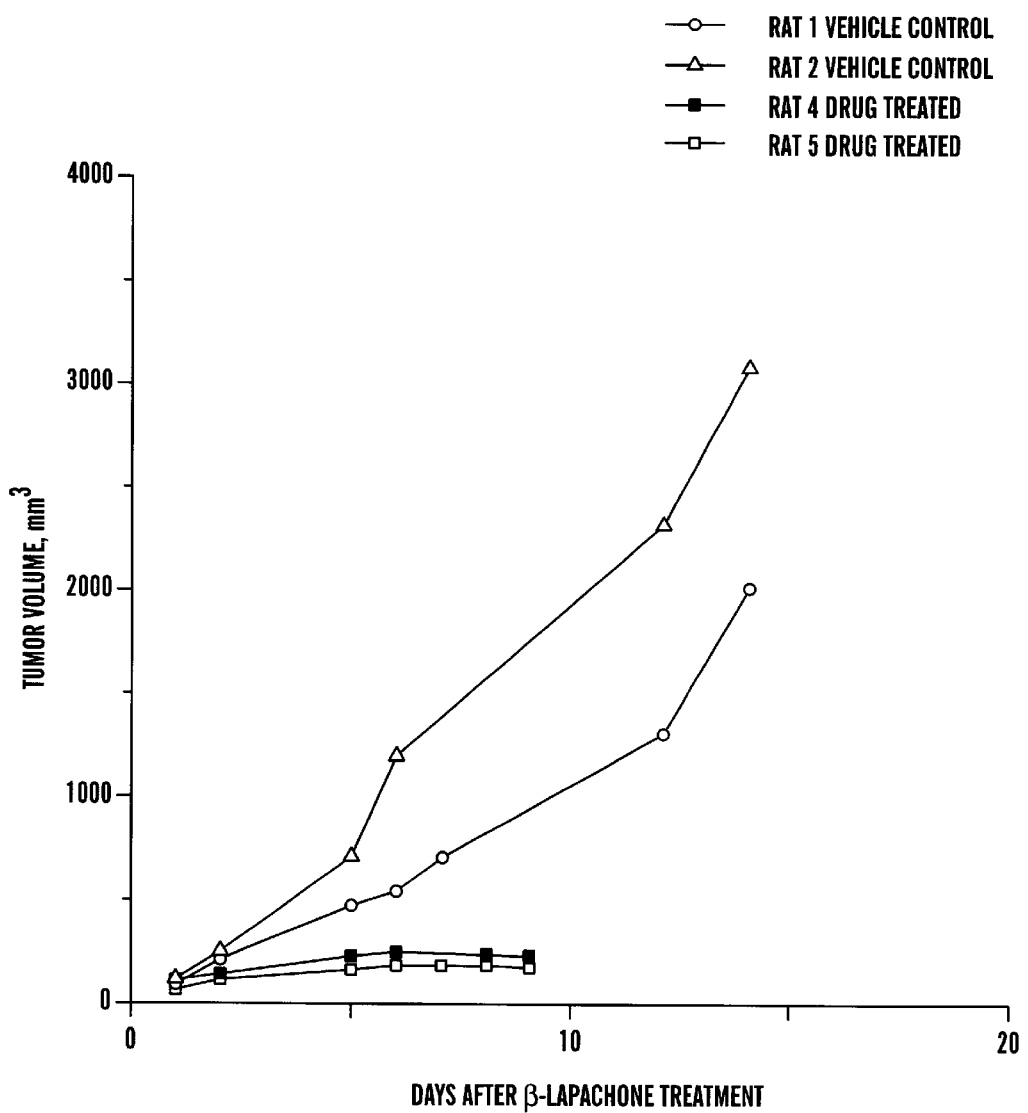
FIG. 6 shows the effect in vivo of β-lapachone on prostate tumors AT-3.1.
Figure 7:
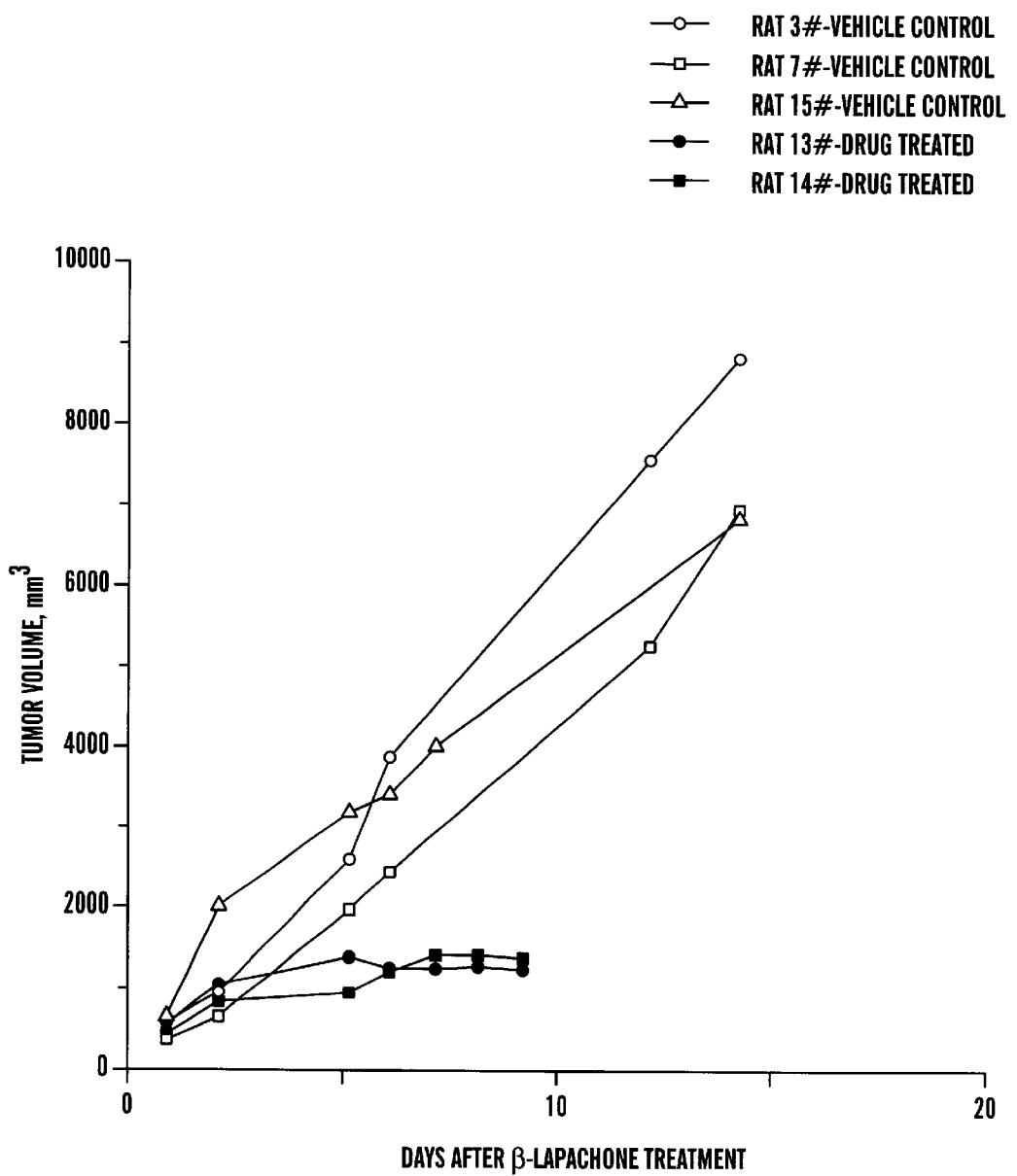
FIG. 7 shows the effect in vivo of β-lapachone on prostate tumors AT-3.1.

In addition, the in vivo efficacy of β-lapachone were determined in a widely used prostate tumor model, Dunning R-3327 rat prostate adenocarcinoma. A highly metastatic and malignant clone (RT-3.1) of Dunning R-3327 prostate adenocarcinoma cells were inoculated into Copenhagen rats. Solid tumor masses were formed one week later. Rats in treatment group received one dose of -lapachone at 50 mg/ml, I.p. Tumor necrosis was observed 24 hours after drug treatment in every treated rats, but not in untreated controls. Tumor volume was measured. The results are set forth in FIGS. 6 and 7.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method of treating androgen independent prostate cancer in a human comprising: selecting a human having androgen independent prostate cancer, and administering to said human an effective amount of a compound of the following formulae I or II to stimulate prostate cell death:

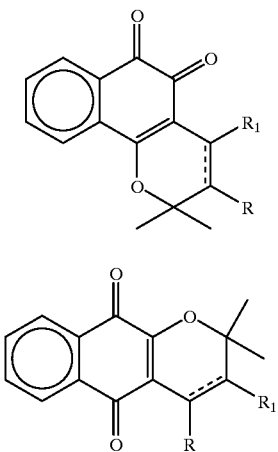

wherein R and $R_1$ are each independently selected from the group consisting of hydrogen, hydroxy, sulfhydryl (SH), halogen, substituted alkyl, unsubstituted alkyl, substituted alkenyl, unsubstituted alkenyl, substituted aryl, unsubstituted aryl, substituted alkoxy unsubstituted alkoxy, and salts thereof, wherein the dotted double bond between the ring carbons to which R and $R_1$ are bonded represent an optional ring double bond.

2. A method of treating benign prostate hyperplasia in a human comprising administering to said human an effective amount of a compound of the following formulae I or II to stimulate prostate cell death:

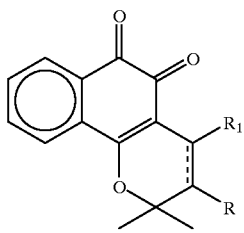

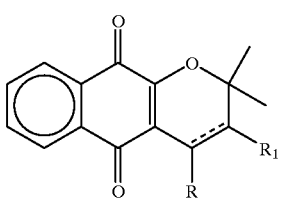

wherein R and $R^1$ are each independently selected from the group consisting of hydrogen, hydroxy, sulfhydryl (SH), halogen, substituted alkyl, unsubstituted alkyl, substituted alkenyl, unsubstituted alkenyl substituted aryl, unsubstituted aryl, substituted alkoxy unsubstituted alkoxy, and salts thereof, wherein the dotted double bond between the ring carbons to which R and $R_1$ are bonded represent an optional ring double bond.

3. The method described in claim 1 or 2, wherein at least one of R and $R_1$ is hydrogen.

4. The method described in claim 1 or 2, wherein at least one of R and $R_1$ is alkenyl.

5. The method described in claim 1 or 2, where at least one of R and $R_1$ is allyl.

6. The method described in claim 1 or 2, where the compound of formula I is selected from the group consisting of β-lapachone, 3-allyl-β-lapachone, 3-OH-β-lapachone and 3-bromo-β-lapachone.

\* \* \* \* \*